United States Patent [19]

Lagunas-Solar

[11] Patent Number: 5,607,711
[45] Date of Patent: *Mar. 4, 1997

[54] METHOD OF CONTROLLING INSECTS AND MITES WITH PULSED ULTRAVIOLET LIGHT

[75] Inventor: Manuel C. Lagunas-Solar, Davis, Calif.

[73] Assignee: The Regents of the University of California, Oakland, Calif.

[ * ] Notice: The term of this patent shall not extend beyond the expiration date of Pat. No. 5,364,645.

[21] Appl. No.: 551,548

[22] Filed: Nov. 1, 1995

[51] Int. Cl.⁶ ..................................................... A23L 3/00
[52] U.S. Cl. ............................................. 426/248; 426/521
[58] Field of Search ................................. 426/248, 238, 426/521; 422/24

[56] References Cited

U.S. PATENT DOCUMENTS

| | | | |
|---|---|---|---|
| 2,784,286 | 3/1957 | Dillon | 47/1.3 |
| 2,856,505 | 10/1958 | Dillon | 219/489 |
| 3,443,051 | 5/1969 | Puschner | 219/748 |
| 3,499,437 | 3/1970 | Balamuth | 47/1.3 |
| 3,753,651 | 8/1973 | Boucher | 219/738 |
| 3,817,703 | 6/1974 | Atwood | 426/248 |
| 3,926,556 | 12/1975 | Boucher | 426/248 |
| 3,941,670 | 5/1976 | Pratt, Jr. | 204/158 R |
| 3,955,921 | 5/1976 | Tensmeyer | 219/121 LM |
| 4,042,325 | 8/1977 | Tensmeyer | 219/121 LM |
| 4,092,800 | 6/1978 | Wayland, Jr. et al. | 47/1.3 |
| 4,201,916 | 5/1980 | Ellner | 250/372 |
| 4,529,489 | 7/1985 | McDonald et al. | 204/158 R |
| 4,590,348 | 5/1986 | Lahti et al. | 219/10.55 M |
| 4,661,264 | 4/1987 | Goudy, Jr. | 422/24 |
| 4,758,318 | 7/1988 | Yoshida | 204/131 |
| 4,871,559 | 10/1989 | Dunn et al. | 426/248 |
| 4,880,512 | 11/1989 | Cornelius et al. | 204/157.61 |
| 5,034,235 | 7/1991 | Dunn et al. | 426/238 |
| 5,059,431 | 10/1991 | Daeschel et al. | 426/13 |
| 5,060,414 | 10/1991 | Wayland | 47/1.3 |
| 5,089,384 | 2/1992 | Hale | 435/2 |
| 5,105,563 | 4/1992 | Fingerson et al. | 34/203 |
| 5,120,450 | 6/1992 | Stanley, Jr. | 210/748 |
| 5,141,059 | 8/1992 | Marsh | 172/1 |
| 5,144,146 | 9/1992 | Wekhof | 210/748 |
| 5,235,043 | 8/1993 | Collins et al. | 530/399 |
| 5,364,645 | 11/1994 | Lagunas-Solar et al. | 426/248 |

*Primary Examiner*—George Yeung
*Attorney, Agent, or Firm*—John P. O'Banion

[57] ABSTRACT

A non-chemical, non-residue method of controlling pests, pathogens and other undesirable organisms found in food supplies. The organisms are exposed to ultra-short pulses of ultraviolet light emitted at a wavelength which is absorbed by surface coloring chemicals in the insect, such as entegumen. The coloring chemicals act as a heat sink to the ultraviolet photons, and the undesired organisms are selectively heated without harming adjacent food objects. The heat thus induced in the insects causes irreparable or irreversible lethal damage.

9 Claims, 1 Drawing Sheet

METHOD OF CONTROLLING INSECTS AND MITES WITH PULSED ULTRAVIOLET LIGHT

BACKGROUND OF THE INVENTION

1. Field of the Invention

This invention pertains generally to controlling or eliminating insects and other undesired organisms, and more particularly to a method of causing irreparable or lethal damage to insects and mites using pulsed ultraviolet light a wavelength which is absorbed by coloring chemicals on the surface of the organisms.

2. Description of the Background Art

Insect controls are a critical need in production and export agriculture as many regulatory barriers such as quarantines impose conditions for transporting foods and agricultural products through regional, national and international boundaries. The use of insecticides and other chemical pesticides is usually the most used technical approach to deal with insect controls.

In the United States, as well as in many other countries, changes in public attitudes towards the use of chemicals to control pests have resulted from increased concern for food safety and preservation of environmental quality. Agricultural pesticides have been used extensively and intensively since the 1940s, resulting in the largest and safest food supply the earth's population has ever seen. However, concerns about this technology have continuously increased as a result of environmental contamination and degradation such as groundwater contamination and ozone depletion, as well as sporadic episodes of acute poisonings. Popular awareness and attitudes concerning these problems are reflected in ever-increasing regulatory actions targeting agricultural pesticides. As the regulations have increased, the availability of agricultural pesticides has decreased. This has imposed new technological demands on agriculture and may create new barriers to the international trade of foods and agricultural commodities because of quarantine regulations of our trading partners capable of targeting specific organisms.

Therefore, there is a need for a non-chemical, non-residue method of efficiently and effectively destroying insects in food supplies. The present invention satisfies that need, as well as others, and overcomes the deficiencies in prior insect control technologies.

SUMMARY OF THE INVENTION

The present invention generally pertains to a method of exposing pests, pathogens and other undesirable organisms found in food supplies with electromagnetic energy in the ultraviolet spectrum wherein the undesired organisms are selectively heated and destroyed without causing damage to the food.

By way of example, and not of limitation, the method of the present invention comprises the steps of exposing insects and other organisms with a plurality of high frequency electromagnetic energy pulses in the ultraviolet spectrum. The wavelength is chosen such that the ultraviolet light is absorbed by surface coloring chemicals in the insect, such as entegumen, which act as a heat sink to the ultraviolet photons. In this manner, the undesired insects are selectively heated without harming adjacent food objects. The heat thus induced in the insects causes irreparable or irreversible lethal damage.

Accordingly, the present invention comprises a non-chemical, non-residue, rapid physical method of destroying insects based upon the use of pulsed and selected monochromatic photons of ultraviolet light which can be generated by lasers or excimer lamps. This method has the capability to replace the use of chemical pesticides, leaves no residue, and can be implemented either in small scale with portable systems or in a larger scale by integrating it to existing technologies capable of handling large amounts of fresh foods and other agricultural commodities such as packaging materials. In addition, because of its physical nature, there is no possibility of insects building-up resistance through genetic changes transferred to new generations as it occurs with most chemical pesticides.

An object of the invention is to expose organisms with short pulses of electromagnetic energy.

Another object of the invention is to generate thermal energy and selectively apply the thermal energy to materials for disinfestation purposes.

Another object of the invention is to effectively apply thermal energy to materials to eliminate or reduce populations of pests and/or pathogens.

Another object of the invention is to selectively heat targeted chemicals and/or organisms through resonance.

Another object of the invention is to selectively heat targeted chemicals and/or organisms with ultraviolet energy without harming adjacent food supplies or desirable organisms.

Another object of the invention is to minimize or eliminate the use of agricultural pesticides to control insects.

Another object of the invention is to provide for in situ elimination of pests and/or pathogens in materials using the photothermal effect.

Another object of the invention is to selectively kill or retard growth of pest and/or pathogen organisms over beneficial organisms.

Another object of the invention is to promote, trigger or synergistically interact with natural processes that inhibit pests and/or pathogens.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
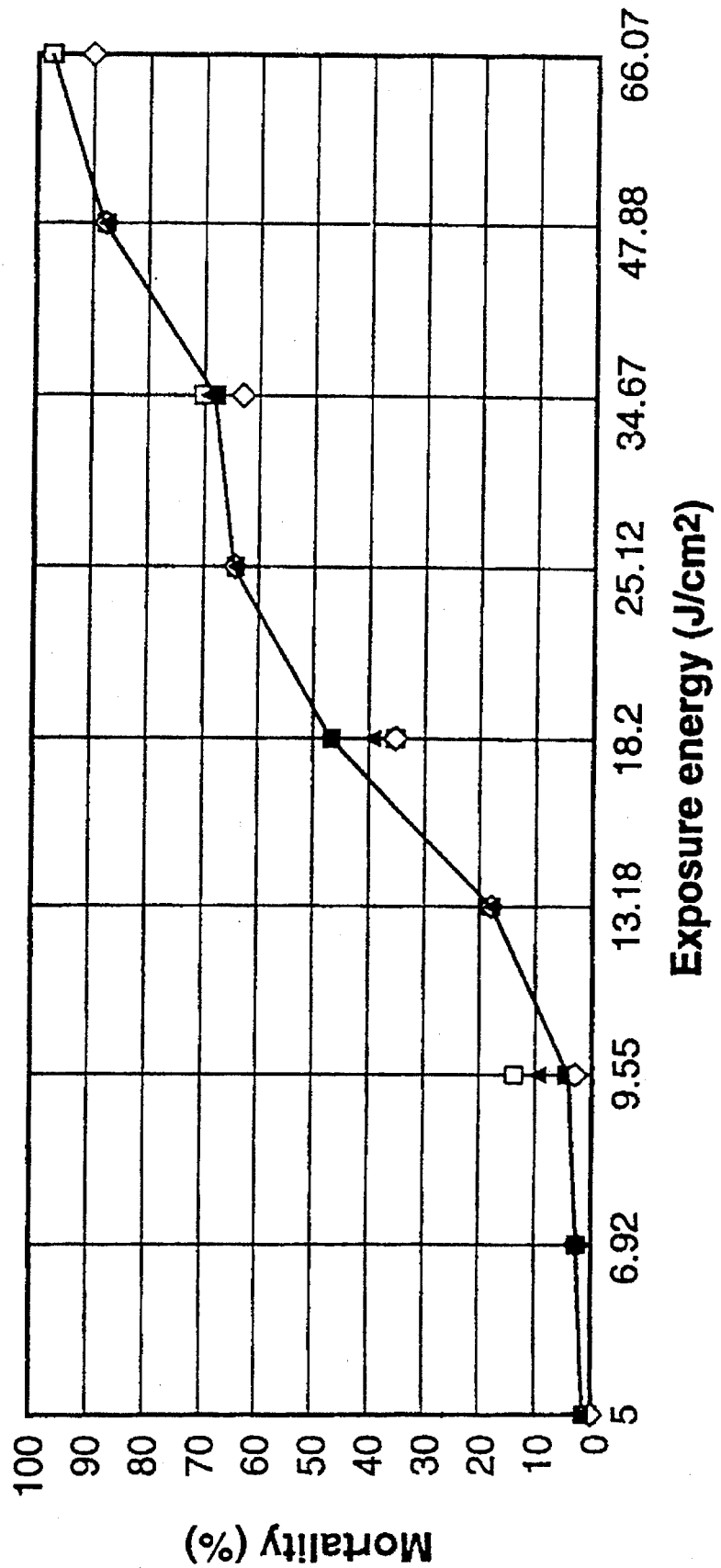
FIG. 1 is a chart showing the mortality rate of Phylloxera eggs as a function of density of energy exposure to ultraviolet light at 308 nanometers.

The interaction between electromagnetic energy and matter depends on the physical properties of the source, as well as the chemical composition of the sample. The thermodynamics and kinetics of the thermally induced chemical reactions taking place in a heated sample depending primarily on the chemical composition of the sample and many physical factors. The amount of absorption of radiant energy of a target sample is a function of both the molecular structure of the same and the physical properties of the radiation such as wavelength. Thus, matching the energy source with the target sample allows specific types of molecules to be electronically excited and irreversible chemical effects can be obtained, including reactions that affect biological functions such as cell division.

In U.S. Pat. No. 5,364,645, which is incorporated herein by reference, it was shown that irradiation of a food object with pulsed ultraviolet lasers causes non-reparable damage to nucleic based structures in microorganisms present in that object without altering the surface properties of the food object. Pulses having a duration ranging from approximately 1 ns to 100 ns, preferably 20 to 30 ns, and energy densities ranging from approximately 0.001 to 2 J/cm$^2$ were shown to be effective for this purpose.

Pulsed irradiation permits use of higher power levels with lower overall energy requirements than with continuous heating and, therefore, is more efficient. Further, use of a pulsed high power source provides for higher temperature heating in a shorter period of time. Thus, at power levels where continuous wave heating would result in atomization of exposed molecules, pulsed irradiation will result in heat transfer without atomization. For pulse outputs in the range of 1 to 2 J/cm$^2$ per pulse, the average power levels can be as high as a few MW/cm$^2$. Irradiation using a plurality of pulses effects a near instantaneous increase in the concentration of thermally excited molecules, while heat dissipation is still sufficiently slow to be destructive to the targeted organisms.

In accordance with the present invention, the targeted organisms are irradiated with a plurality of pulses of ultraviolet energy. Rather than targeting DNA as in U.S. Pat. No. 5,364,645, the wavelength is chosen such that selected photons in the 200–400 nm ultraviolet region, and preferably 210 to 350 nm ultraviolet region, are absorbed selectively by certain coloring chemicals, such as entegumen, typically present on the surface of insects. It has been found that these "melamine-like" chemicals are highly absorbent to ultraviolet light, and act as "heat sinks" which rapidly convert the ultraviolet energy into thermal energy creating small areas of intense heat that cannot be dissipated and which cause irreparable or irreversible lethal damage to the organism. These effects have been demonstrated in all stages of biological development of insects, such as eggs, pupae, larvae, and adults.

Significantly, it has been found that selected wavelengths in the ultraviolet energy spectrum work better than others due to resonance characteristics of the different chemicals on the insects' entegumen. Targeting the insects with selected narrow-band (monochromatic or nearly monochromatic) wavelengths of ultraviolet photons in the 210 nm to 350 nm region may also allow for selection of the types of insects to be affected. In particular, it has been found that melamine pigment absorption peaks at 222 nm.

The effect of applying ultraviolet radiation in accordance with the present invention is rapid and irreversible because the exposure to selected ultraviolet photons occurs in extremely short bursts, or pulses, of ultraviolet light lasting less than a microsecond. Therefore the addition of even small amounts of energy, such as less than one millijoule, still produces instant heat with power levels into the kilowatt or Megawatt levels since one megawatt is equal to one millijoule per nanosecond. The conversion of ultraviolet energy to thermal energy on a specific ultraviolet absorbing area such as targeted coloring pigments produces intense, nearly instantaneous heat. Biological systems are not capable of rapidly dissipating these heat power levels and therefore biological structures are destroyed.

For example, where pulses having energies ranging from 200 to 400 millijoules per pulse and a pulse duration of less than 10 ns are generated from a monochromatic or nearly monochromatic energy source such as excimer lasers or lamps, and assuming 100% conversion to thermal energy, heat will be generated in the range of approximately 20 to 40 MW per pulse. Because these excimer technologies can operate reliably with hundreds of pulses per second in the case of excimer lasers, and thousands of pulses per second in the case of excimer lamps, extremely high thermal power can be produced and be sufficient to scan large areas suspected to contain insects, mites, eggs or other targets quickly and with high efficiency.

EXAMPLE 1

In order to demonstrate the efficacy of using pulsed ultraviolet to control insect populations, we selected a variety of insects, mites and insect eggs to irradiate with two monochromatic sources; 248 nm from a Lambda Physik EMG-150 KrF excimer laser, and 308 nm from a Lambda Physik EMG101MSC ExCl excimer laser. The samples were exposed using a variety of experimental setups. Some samples were exposed to the direct beam from the laser (for high power densities; 100 millijoules/cm$^2$), while other samples were exposed to an expanded beam from either a diverging leans or a telescopic setup (for low power densities; <1 millijoule/cm$^2$).

EXAMPLE 2

Coleoptera were subjected to 1 to 2 pulses of collimated ultraviolet laser beam at 248 nm with approximately 100 mJ/cm$^2$ pulses. The Coleoptera exposed to 2 pulses died almost instantaneously as a result of massive heat damage. The heat damage was clearly seen under magnification (stereoscope 30x) and indicated clear evidence of oxidation (browning), charring (antennas) and the disappearance of clear pigmented areas in the entegumen.

EXAMPLE 3

A group of Homoptera ranging from several mm to 1 to 2 cm in size were exposed to 1 to 3 pulses of ultraviolet light at 248 nm with approximately 108 mJ/cm$^2$ pulses. Magnified observations yielded results similar to those observed for Coleoptera. Death occurred almost instantaneously for most of these samples as a result of heat induced damage as evident from browning (oxidation) effects.

EXAMPLE 4

Ants approximately 4 to 6 mm long were treated with 10 pulses from an expanded ultraviolet laser beam at 248 nm with approximately 0.8 mJ/cm$^2$ pulses. The ants exploded briefly after exposure.

EXAMPLE 5

Phylloxera eggs less than 1 mm in size, and adults of *Tetranychus urticae* (spider mite) approximately 1 mm in size, were treated on leaves with energies ranging from 25 mJ/cm$^2$ to 2.3 J/cm$^2$ from a pulsed ultraviolet laser at 308 nm. Twenty-four hours after exposure there was up to a 90% decrease in the adult population. Treated eggs appeared oxidized (browning) due to heat deposition.

EXAMPLE 6

Phylloxera eggs less than 1 mm in size were exposed to an expanded beam (diverging lens) from a pulsed ultraviolet laser at 308 nm. The eggs suffered a 70% mortality with an exposure of 34.7/cm$^2$. Increasing the exposure to 66 J/cm$^2$ resulted in a mortality greater than 97% for all samples. FIG. 1 shows the effect of mortality rate as a function of exposure energy for three different experiments, with each different symbol (triangle, open box, solid box) on the graph representing a different experiment.

EXAMPLE 7

Hemiptera eggs approximately 1 mm in size were treated with 1 to 5 pulses of 238 nm ultraviolet photons from an excimer laser. The eggs showed browning effects. No egg hatched.

EXAMPLE 8

*Brevipalpus chilensis* (similar to *Brevipalpus californicus*) mites less than 0.1 mm in size were exposed to a direct beam from a pulsed ultraviolet laser at 248 nm. The total exposure was progressively increased while making intermediate observations until the whole population was killed. Depending on the size and maturity of the population, the necessary energy for complete control varied from 38.5 mJ/cm$^2$ to 79.5 mJ/cm$^2$.

EXAMPLE 9

Tables 1 and 2 summarize experimental conditions and results of insect control in accordance with the present invention.

The experiments summarized in Examples 1 through 8 and Tables 1 and 2 demonstrate that pulsed ultraviolet light is effective for control of insects and mites, not only over a wide a variety of species, but for a variety of developmental stages. Accordingly, it can be seen that the present invention provides for the efficient and effective control of organisms with pulsed ultraviolet light at a wavelength wherein the ultraviolet light is absorbed by coloring chemicals on the surface of said organism and wherein absorption of said ultraviolet light causes lethal damage to said organism by conversion of said ultraviolet light into thermal energy without alteration of the surface properties of adjacent food objects. The melamine-like coloring pigments that are characteristic of the particular insect being controlled are targeted as heat sinks for the ultraviolet radiation. In essence, the irradiation becomes lethal to the insect as a result of the "resonance" effect on the coloring pigments, as well as the phothermic effect of rapid energy input. It will also be appreciated that part of the nervous system and vision is often on the surface of an insect; However, the surface structure of the insect is affected without necessarily affecting the nervous system although the sensory inputs of the insect such as vision and smell may be affected.

Although the description above contains many specificities, these should not be construed as limiting the scope of the invention but as merely providing illustrations of some of the presently preferred embodiments of this invention. Thus the scope of this invention should be determined by the appended claims and their legal equivalents.

TABLE 1

| Species | Wavelength (nm) | Energy/pulse | Energy Density | Result |
| --- | --- | --- | --- | --- |
| Ants | 248 | 20 mJ/pulse | 8 mJ/cm$^2$ pulse | insect "blown up" and died |
| Bemecia Tabaci | 248 | 325 mJ/pulse | 108 mJ/cm$^2$ | insect curled and died |
| Aleyrodidae Homoptera | 248 | 325 mJ/pulse | 108 mJ/cm$^2$ | wings curled, eyes darker, insect died |
| Coleoptera (Lady Bug) | 248 | no data | 100 mJ/cm$^2$ | oxidation, charring of antennas, disappearance of clear pigmented areas in the entegumen, insect died |
| Phylloxera eggs | 308 | 29 mJ/pulse | 3.3 mJ/cm$^2$ pulse<br>60 J/cm$^2$ | 18 × 10$^3$ pulse<br>100% mortality |
| Phylloxera eggs | 308 | 27 mJ/pulse | 3.1 mJ/cm$^2$ pulse<br>66.1 J/cm$^2$ | 21 × 10$^3$ pulses<br>97% mortality |
| Phylloxera eggs | 308 | 24 mJ/pulse | 2.7 mJ/cm$^2$ pulse<br>34.7 J/cm$^2$ | 13 × 10$^3$ pulses<br>70% mortality |
| Brevipalpus chilensis | 248 | 116 mJ/pulse | 17.1 mJ/cm$^2$<br>57 mJ/cm$^2$ | 50% mortality<br>100% mortality |
| Brevipalpus chilensis | 248 | 107 mJ/pulse | 15.9 mJ/cm$^2$<br>53 mJ/cm$^2$<br>79.5 mJ/cm$^2$ | 50% mortality<br>83% mortality<br>100% mortality |
| Brevipalpus chilensis | 248 | 112 mJ/pulse | 5.5 mJ/cm$^2$<br>16.5 mJ/cm$^2$<br>38.5 mJ/cm$^2$ | 86% mortality<br>94% mortality<br>100% mortality |

TABLE 2

1. Stink bug (eggs & adults) Bletforia (cockroach) nimphe

| | |
| --- | --- |
| Wavelength: | 248 nm |
| Energy: | 690 mJ/pulse |
| Area: | 28 cm$^2$ |
| Results: | Eggs sterilized (no hatching); adults dead. |

2. Lady Bug (Coleoptera)

| | |
| --- | --- |
| Wavelength: | 248 nm |
| Density: | 100 mJ/cm$^2$ |
| Pulses: | 1 to 2 |
| Results: | Insect died. Charring of antennas. Disappearance of clear pigmented areas in the entegumen. |

TABLE 2-continued

3. Yellow Aphid Tenebriod Chrysonelid Rose Aphid

Exposure experiments done with and without telescope
Some of the numbers are inconsistent

| | |
|---|---|
| Energy: | 8 mJ/pulse. |
| Density: | After handiwrap covering accounted for 0.5 mJ/cm² pulse |
| Yellow Aphid | 100 mJ/cm–500 mJ/cm² |
| Tenebriod | 1 J/cm²–5 J/cm² |
| Chrysonelid (Lady Bug) | 0.5 J/cm²–1 J/cm² |
| Rose Aphid | 100 mJ/cm²–500 mJ/cm² |
| Results: | No observations. |

4. *Tetranychus urticae* mite (spider mite)

| | | |
|---|---|---|
| Wavelength: | | 248 nm |
| (a) Exp 1: | | |
| | Energy: | 24 mJ/pulse |
| | Density: | 1.1 mJ/cm² |
| | Pulses: | 20 to 100 |
| | Results: | No observations. These data may refer to next "Experiment." |
| (b) Exp 2: Different energy levels: | | |
| | Density: | 25 mJ/cm² 68 eggs 40 adults |
| | Results: | After 24 hours, ~4–5 adults are alive (little movement); |
| | Density: | 50 mJ/cm² 42 adults 72 eggs |
| | Results: | After 24 hours, a few adults still alive (may have been protected by the leaves) |
| | Density: | 125 mJ/cm² 66 adults 72 eggs |
| | Results: | After 24 hours, 5–6 adults are alive, 60 dead |
| | Density: | 75 mJ/cm² 7 adults 100 eggs |
| | Results: | After 24 hours, 1 out of 7 adults alive. Little movement |
| | Density: | 125 mJ/cm² 5 adults 70 eggs |
| | Results: | After 24 hours, 10–12 adults alive |
| | Density: | 1.4 mJ/cm² 32 eggs 14 adults |
| | Results: | After 24 hours, 3 adults moving |
| | Density: | 250 mJ/cm² 16 eggs 3 adults |
| | Results: | After 24 hours eggs not affected, 1 adult alive |
| | Density: | 2.3 mJ/cm² 48 eggs |
| | Results: | After 24 hours, 6 moving adults |

5. *Bemesia Tabaci*

| | |
|---|---|
| Wavelength: | 248 nm |
| Energy: | 325 mJ/pulse. |
| Results: | After one pulse the insect "curled up" and died one minute after laser application |

6. *Aleyrodidae Homoptera* (Sweet Potato white fly)

| | |
|---|---|
| Wavelength: | 248 nm |
| Energy: | 325 mJ/pulse. |
| Results: | After one pulse the insect wings curled; eyes may be darker; insect died. |

7. Ash White Fly

| | |
|---|---|
| Wavelength: | 248 nm |

Treated on Poinsettia (*Euphorbia Eulcherrima*).

| | |
|---|---|
| Energy: | 22 mJ/pulse |
| Density: | 1 mJ/pulse cm² |
| Pulses: | 5 to 300 |
| Results: | No observations recorded |

8. Ants

| | |
|---|---|
| Wavelength: | 248 nm |

One set of experiments, the ants were slowed down in freezer. All died including controls. Another experiment, ants "blown up." Expanded beam approximately 20 mJ/pulse, 0.8 mJ/cm², approximately 10 pulses.

9. Fruit Fly (Assumed; not identified)

| | |
|---|---|
| Wavelength: | 248 nm |
| Energy: | 18.5 mJ/pulse |
| Pulses: | 3–27 |
| Results: | No observed effect |

10. Phylloxera eggs

| | |
|---|---|
| Wavelength: | 308 nm |
| Energy/egg | $2.3 \times 10^{-2}$ mJ to $40.5 \times 10^{-2}$ mJ |
| Results: | No effect |
| Wavelength: | 308 nm |
| Energy/egg | 13.6 mJ - 68% mortality >27.2 mJ - 100% mortality |
| Comparison with Low-pressure Continuous UV (Hg lamp) | |
| Energy/egg | $2.4 \times 10^{-3}$ mJ to $2.4 \times 10^{-2}$ mJ - no effect $8.1 \times 10^{-2}$ mJ 20% mortality |
| Wavelength: | 308 nm |
| Energy/egg | 2.2 mJ - 2% mortality 29.8 mJ - 97% mortality |
| Comparison with Low-pressure Continuous UV (Hg lamp) | |
| Energy/egg | $3.1 \times 10^{-2}$ mJ to $23 \times 10^{-2}$ mJ - no effect |
| Wavelength: | 308 nm |
| Energy/egg | 1.7 mJ–10.2 mJ |
| Results: | No results reported |
| Comparison with Low-pressure Continuous UV (Hg lamp) | |
| Energy/egg | $2.4 \times 10^{-2}$ mJ to $15 \times 10^{-2}$ mJ - no results reported |
| Wavelength: | 308 nm |
| Energy/egg | 2.2 mJ–29.8 mJ - no results reported |
| Comparison with Low-pressure Continuous UV (Hg lamp) | |
| Energy/egg | $10 \times 10^{-2}$ mJ to $240 \times 10^{-2}$ mJ - no results reported |
| Wavelength: | 308 nm |
| Energy/egg | 8.2 mJ (38.5 mortality) 15.7 mJ (70.4% mortality) |
| Comparison with Low-pressure Continuous UV (Hg lamp) | |
| Energy/egg | $10 \times 10^{-2}$ mJ 29% mortality $240 \times 10^{-2}$ mJ 98.9% mortality |

11. *Brevipalpus chilensis*

| | |
|---|---|
| Wavelength: | 248 nm |
| Nr. of mites - 6 | |
| Density | 5.7 mJ/cm² mortality - 0% 17.1 mJ/cm² mortality - 50% 57 mJ/cm² mortality - 100% |
| Wavelength: | 248 nm |
| Nr. of mites - 6 | |
| Density | 5.3 mJ/cm² mortality - 0% 15.9 mJ/cm² mortality - 50% 53 mJ/cm² mortality - 83% 79.5 mJ/cm² mortality - 100% |
| Wavelength: | 248 nm |
| Nr. of mites - 35 | |
| Density | 5.5 mJ/cm² mortality - 86% 16.5 mJ/cm² mortality - 94% 38.5 mJ/cm² mortality - 100% |

What is claimed is:

1. A method of causing irreparable or irreversible lethal damage to an undesirable organism, comprising the step of irradiating an undesired organism with a plurality of ultraviolet light pulses at a wavelength wherein said ultraviolet light is absorbed by coloring chemicals on the surface of said organism and wherein said absorption of said ultraviolet light causes lethal damage to said organism by conversion of said ultraviolet light into thermal energy.

2. A method as recited in claim 1, further comprising the step of generating narrow band ultraviolet light at a wavelength between approximately 200 nm and 400 nm.

3. A method as recited in claim 1, wherein said light pulses have a duration ranging from approximately 1 ns to 100 ns.

4. A method of controlling undesired organisms on the surface of food objects, comprising the step of irradiating an undesired organism with a plurality of ultraviolet light pulses at a wavelength wherein said ultraviolet light is absorbed by coloring chemicals on the surface of said organism and wherein said absorption of said ultraviolet light causes lethal damage to said organism by conversion of said ultraviolet light into thermal energy without alteration of the surface properties of adjacent food objects.

5. A method as recited in claim 4, further comprising the step of generating narrow band ultraviolet light at a wavelength between approximately 200 nm and 400 nm.

6. A method as recited in claim 5, wherein said light pulses have a duration ranging from approximately 1 ns to 100 ns.

7. A method of controlling undesired organisms without altering the visual appearance of food surfaces, comprising the step of irradiating the surface of a food object containing an undesired organism with a plurality of ultraviolet light pulses at a wavelength wherein said ultraviolet light is absorbed by coloring chemicals on the surface of said organism and wherein said absorption of said ultraviolet light causes lethal damage to said organism by conversion of said ultraviolet light into thermal energy without alteration of the surface properties of said food object.

8. A method as recited in claim 7, further comprising the step of generating narrow band ultraviolet light at a wavelength between approximately 200 nm and 400 nm.

9. A method as recited in claim 8, wherein said light pulses have a duration ranging from approximately 1 ns to 100 ns.

\* \* \* \* \*